(12) United States Patent
Davis et al.

(10) Patent No.: US 7,134,352 B2
(45) Date of Patent: Nov. 14, 2006

(54) METHOD AND APPARATUS FOR EXAMINING OBSTRUCTED WELDS

(75) Inventors: Trevor Davis, Charlotte, NC (US); Jack Matsumoto, Sunnyvale, CA (US)

(73) Assignee: General Electric Company, Schenectady, NY (US)

( * ) Notice: Subject to any disclaimer, the term of this patent is extended or adjusted under 35 U.S.C. 154(b) by 117 days.

(21) Appl. No.: 10/848,371

(22) Filed: May 13, 2004

(65) Prior Publication Data

US 2005/0252313 A1  Nov. 17, 2005

(51) Int. Cl.
*G01M 19/00* (2006.01)
*G21C 17/00* (2006.01)
*G21C 17/003* (2006.01)

(52) U.S. Cl. .................. 73/865.8; 73/618; 73/620; 73/634; 73/640; 376/249

(58) Field of Classification Search ............... 73/865.8, 73/618–623, 634, 635, 637, 638, 640; 376/249
See application file for complete search history.

(56) References Cited

U.S. PATENT DOCUMENTS

| | | | | |
|---|---|---|---|---|
| 4,299,656 A | * | 11/1981 | Weber et al. ............... 376/249 |
| 4,404,853 A | * | 9/1983 | Livingston ................... 73/622 |
| 5,571,968 A | * | 11/1996 | Buckley ...................... 73/623 |
| 5,586,155 A | * | 12/1996 | Erbes et al. ................ 376/249 |
| 6,332,011 B1 | * | 12/2001 | Johnson ...................... 376/249 |
| 6,414,458 B1 | * | 7/2002 | Hatley et al. .......... 318/568.12 |
| 2003/0047585 A1 | * | 3/2003 | McCombe et al. ........ 228/49.1 |
| 2005/0056105 A1 | * | 3/2005 | Delacroix et al. ......... 73/865.8 |

* cited by examiner

*Primary Examiner*—Daniel S. Larkin
(74) *Attorney, Agent, or Firm*—Harness, Dickey & Pierce

(57) ABSTRACT

A method and apparatus is provided for inspecting material arranged within an annular recess such as weld beads, particularly weld beads between the shroud, core plate and support structures within a boiling water nuclear reactor (BWR). The apparatus comprises a track support, a generally arcuate track, a carriage, a sensor support and a sensor. The track is configured to correspond and align generally with an inner surface of a shroud or other encompassing structure with the sensor support and sensor configured to be extended into and then moved horizontally along the annular recess. The sensor may be configured with a plurality of sensor elements, such as ultrasonic transducers or eddy current sensors that may be configured to analyze different properties or different regions relative to the sensor location.

20 Claims, 7 Drawing Sheets

METHOD AND APPARATUS FOR EXAMINING OBSTRUCTED WELDS

BACKGROUND OF THE INVENTION

This invention relates generally to the in situ and non-destructive examination of large circumferential surfaces, particularly including welds, and more particularly, obstructed and recessed peripheral welds. Such surfaces and welds may be found throughout boiling water nuclear reactors and, in particular, welds between ring structures that support the core plate and the core shroud arranged above the ring structures, sometimes referred to as the H6A weld.

A reactor pressure vessel (RPV) of a boiling water reactor (BWR) typically has a generally cylindrical shape and is closed at both ends, e.g., by a bottom head and a removable top head. A top guide, sometimes referred to as a grid, is spaced above a core plate within the RPV. A core shroud, or shroud, surrounds the core plate and is supported by a shroud support structure. The core shroud is a reactor coolant flow partition and structural support for the core components. In most instances, the core shroud will have a generally cylindrical shape and surround both the core plate and the top guide. A removable shroud head is coupled to a shroud head flange at the top of the shroud.

Above the H6A weld, the core plate will typically be spaced from the shroud using a series of irregularly spaced core plate wedges set into a thin annular opening formed between the core plate and the inner surface of the shroud. The core plate wedges obstruct access to the welds and surfaces within the annular opening and the irregular spacing between the core plate wedges further complicates access. During operation of the reactor, however, the circumferential weld joints may experience intergranular stress corrosion cracking (IGSCC) and irradiation-assisted stress corrosion cracking (IASCC) in weld heat affected zones which can diminish the structural integrity of the welds. In particular, lateral seismic/dynamic loading could cause relative displacements at cracked weld locations and may produce leakage and misalignment of reactor components that could compromise the safety or performance. Given the complex configuration of the attachment between the shroud and core plate, however, in situ examination of the welds has proven very difficult.

It is desirable, therefore, to provide an apparatus and a corresponding method for inspecting the welds used to attach the shroud and the core plate to support rings arranged below the core plate that is reliable and is capable of examining the majority of the circumference of such welds and the associated surfaces. When using ultrasonic sensors to examine a weld, the focus point, direction and frequency of the ultrasonic beam may be selected to align with a predetermined fusion line between a weld and the attached structures. The ultrasonic beam may then be repeatedly refocused to move the focal point along the weld fusion line in discrete increments of about 0.25 to about 12.7 mm (about 0.01 to about 0.5 inch). One method for such incremental scanning is disclosed in U.S. Pat. No. 6,332,011, the contents of which are hereby incorporated by reference.

A variety of mechanisms have been devised for the examination of welds, particularly for use in hostile environments such as the interior of RPVs. One such apparatus is disclosed in U.S. Pat. No. 5,568,527, the contents of which are hereby incorporated by reference, and provides a remotely operated apparatus with clamping, sliding, rotational and sensor mechanisms to scan an ultrasonic transducer over specific core spray "T-box" welds including the T-box to cover plate attachment the T-box to thermal sleeve attachment welds.

BRIEF SUMMARY OF THE INVENTION

In an exemplary embodiment, an apparatus is provided for inspecting a majority of the length of one or more obstructed welds used in attaching the shroud and the core plate to supporting structures. The exemplary apparatus may be embodied in a range of configurations, but will tend to include a support, a frame which may include integral holding means, a connector, a carrier and a sensor. In an exemplary embodiment, the disclosed apparatus is positioned adjacent a portion of the inner surface of the shroud near the core plate and temporarily held in place. The sensor is positioned sufficiently close to the weld or surface of interest and activated, either continuously or in a pulsed fashion, as carrier moves, either continuously or in a stepwise or incremental fashion, along the frame to move the sensor(s) along the scanned feature to acquire data corresponding to the character and quality of scanned feature.

BRIEF DESCRIPTION OF THE DRAWINGS

Exemplary embodiments of the devices and methods that may be utilized to practice the present invention are addressed more fully below with reference to the attached drawings in which.

It should be noted that these Figures are intended to illustrate the general characteristics of methods and materials of exemplary embodiments of this invention, for the purpose of the description of such embodiments herein. These drawings are not, however, to scale and may not precisely reflect the characteristics of any given embodiment, and should not be interpreted as defining or limiting the range of values or properties of embodiments within the scope of this invention. In particular, the relative sizing and positioning of the various elements may be reduced or exaggerated for clarity.

DETAILED DESCRIPTION OF THE INVENTION

Figures 1A, 1B:
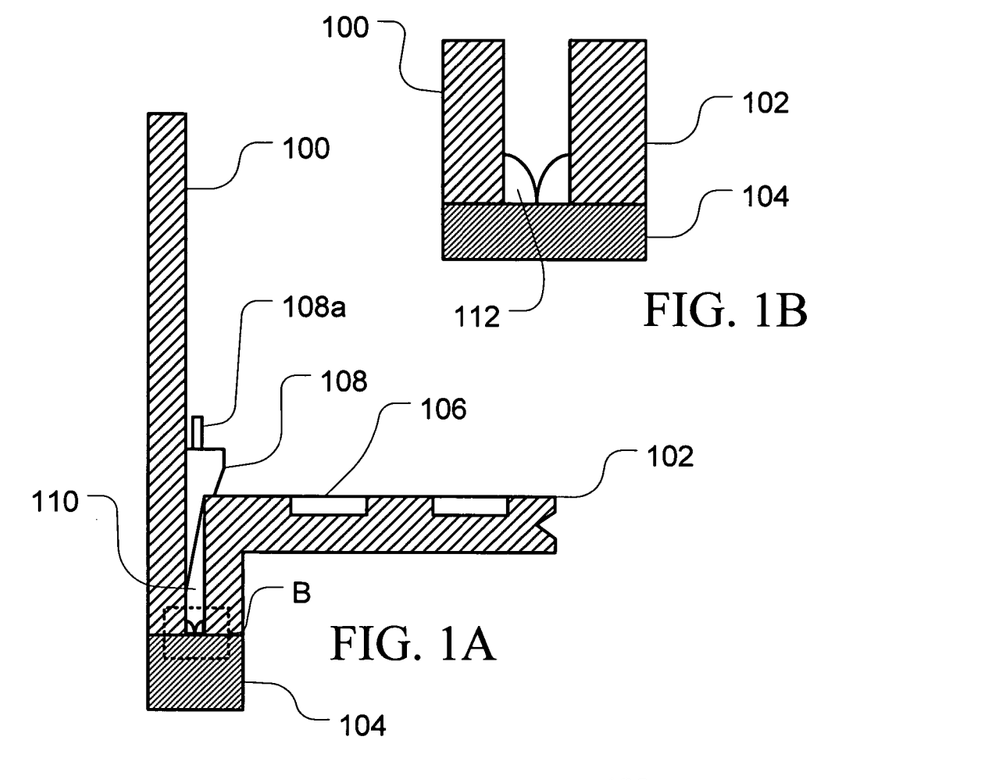
FIG. 1A is a sectional view of a region of a typical boiling water nuclear reactor (BWR) pressure vessel at the junction of the shroud and the core plate.
FIG. 1B is a sectional view of the region B providing an enlarged illustration of the attachment between the shroud, the core plate and a support member.

FIG. 1A is a partial sectional view of a portion of a boiling water nuclear reactor (BWR) pressure vessel (RPV). RPV typically have a generally cylindrical shape that is closed at one end by a bottom head and at its other end by a removable top head with a side wall extending between the bottom head and the top head. Within the RPV will be arranged a generally cylindrically shaped core shroud 100 that surrounds the reactor core in which fuel bundles will be supported by a core plate 102 having receiving recesses 106 arranged on a top surface. The shroud 100 will be supported at one end by a shroud support 104 and will typically include a removable shroud head at the other end. An annular gap 110 is formed between shroud 100 and the core plate 102 into which a series of core plate wedges 108, which may include handling loops 108a, are partially inserted into the annular gap to control the relative positioning of the shroud and the core plate.

The amount of heat generated in the reactor core is regulated by inserting and withdrawing control rods of neutron absorbing material such as, for example, hafnium. To the extent that control rods are inserted into the fuel bundles, the control rods will absorb neutrons that would otherwise be available to promote the chain reaction which generates heat in the reactor core. Control rod guide tubes may be used to maintain the vertical motion of control rods during insertion and withdrawal and control rod drives may be used for selectively inserting and withdrawing the control rods during the operation of the reactor. The fuel bundles may be aligned using the core plate 102 and the receiving recesses 106 or other alignment structure to control the spacing and stabilize the fuel bundles. A top guide plate may also be used for aligning the fuel bundles as they are lowered into the reactor core.

Welds between the shroud, the shroud support and the core plate may encompass a variety of different "standard" configurations depending on the particular generation of BWR, the equipment vendor and the contractor. In certain BWR installations, both the shroud 100 and the core plate 102 will be welded to the shroud support 104 with welds 112 that are positioned at the lower end of the annular gap 110 formed between the shroud and the core plate as illustrated in FIG. 1B.

Figure 1C:
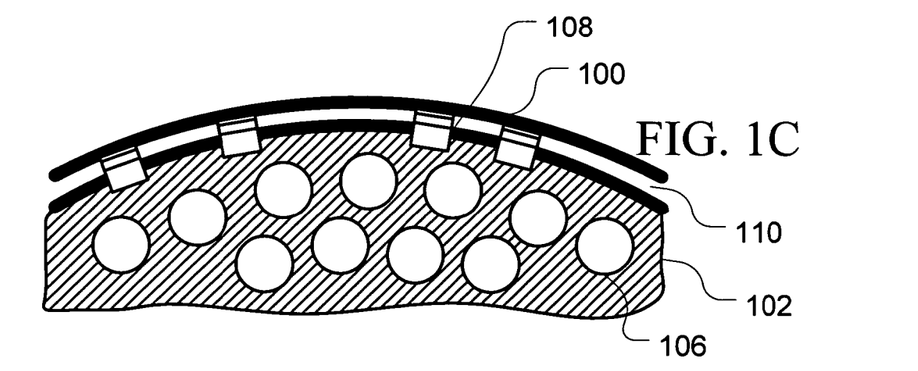
FIG. 1C is a plan view of the region illustrated in FIGS. 1A–B.

As illustrated in FIGS. 1A–C, the small annular space or gap 110 formed between the shroud and the core plate, which may have a width of only about 13 mm (0.5 inch), and the presence of the core plate wedges 108, hampers access to the welds 112 and renders the necessary installation and in service inspections of the welds a serious challenge.

Figure 2A:
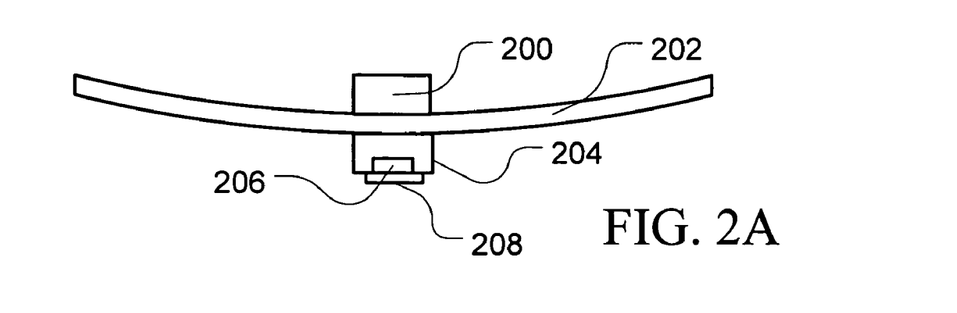
FIGS. 2A–C are plan views illustrating the operation of certain elements of an exemplary embodiment of the invention.
Figure 2B:
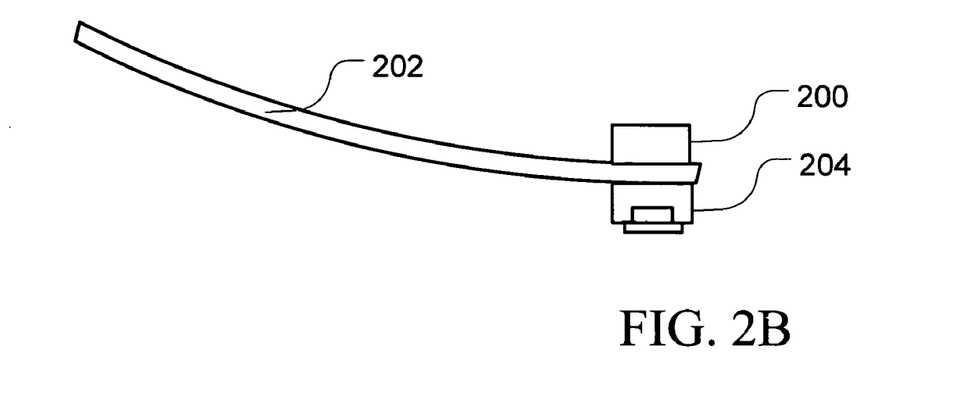
Figure 2C:
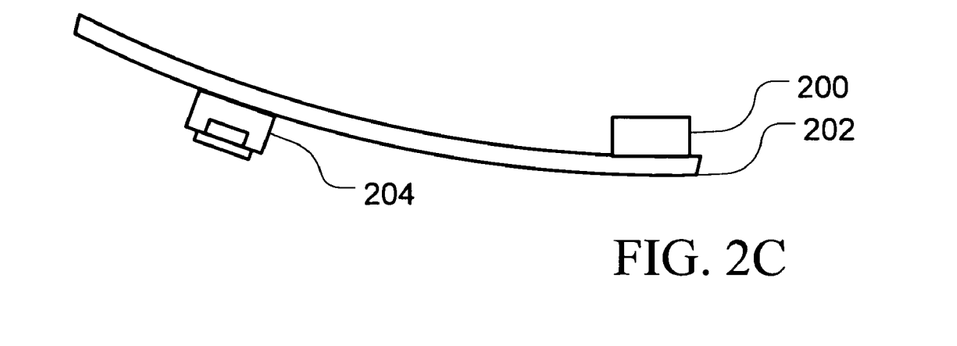

FIGS. 2A–2C illustrate the operation some of the basic components of an exemplary apparatus according to the present invention. As illustrated, a track support 200 supports an arcuate track 202 that, in turn, supports a scanning assembly on its outer face that includes a carriage 204, a sensor support 206 and a sensor 208 and mechanisms that provide for the relative movement of the various elements (not illustrated). As illustrated in FIG. 2B, the track support 200 may be arranged and configured for repositioning the arcuate track in an offset or cantilevered position relative to the track support. Similarly, as illustrated in FIG. 2C, the scanning assembly may be moved along the arcuate track 202 in order to position the sensor 208 for scanning and to conduct the scan.

Figure 3A:
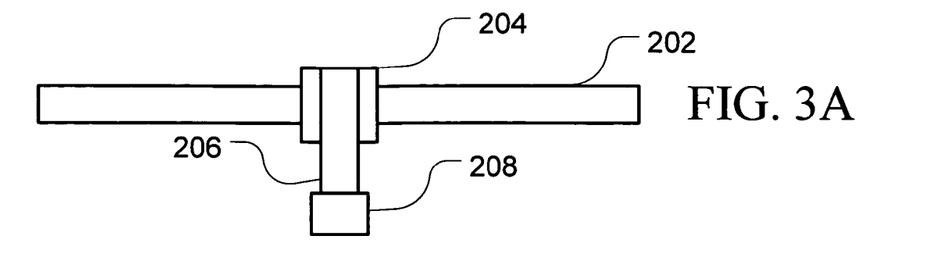
FIGS. 3A–D are views illustrating the operation of certain elements of an exemplary embodiment of the invention.
Figure 3B:
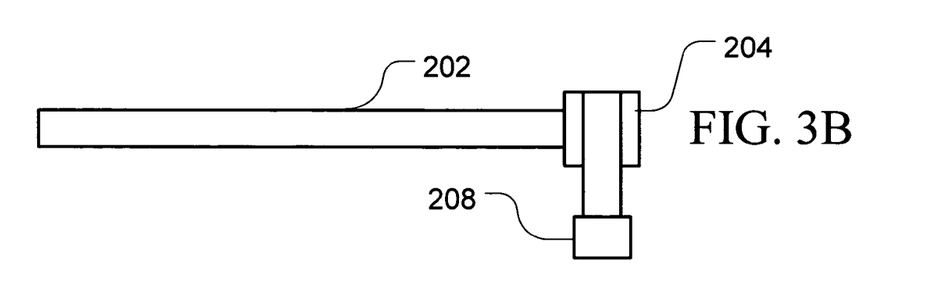
Figure 3C:
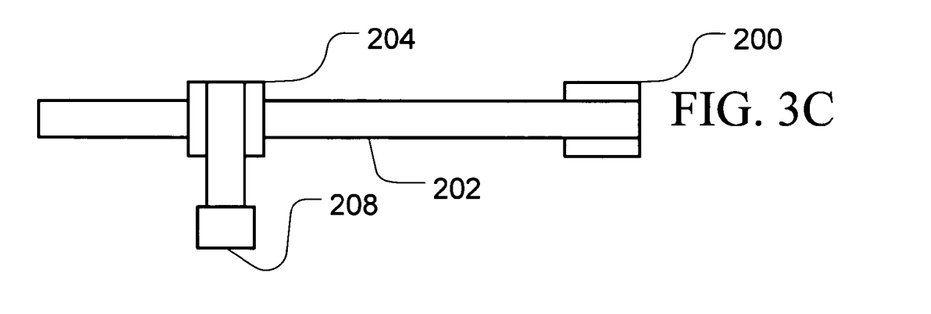
Figure 3D:
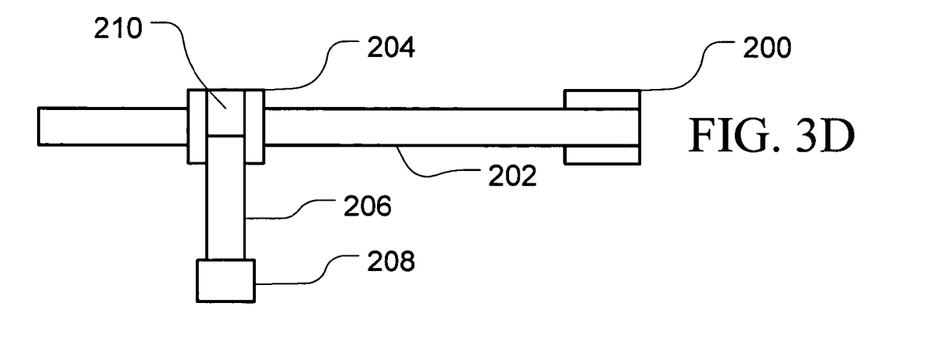

The operation of the basic components illustrated in FIGS. 2A–C and described above are substantially duplicated in FIGS. 3A–C. As reflected in FIG. 3D, however, the sensor support 206 may also be moved vertically relative to the arcuate track 202 utilizing a track or guide 210 for the purpose of inserting the sensor 208 into the annular gap 110 and positioning it in sufficient proximity to the welds 112 or one of the side surfaces of the shroud 100 or core plate 102 to allow for the desired scanning operation to be conducted.

Figure 4A:
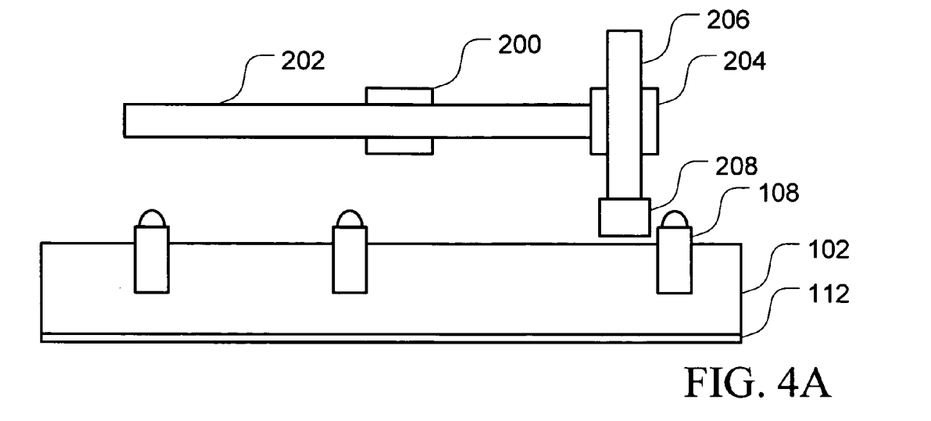
FIGS. 4A–C are views illustrating the operation of certain elements of an exemplary embodiment of the invention during a scanning operation.
Figure 4B:
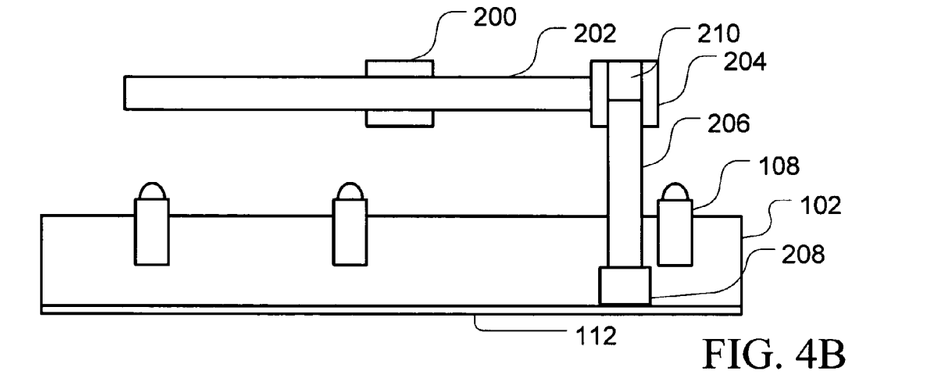
Figure 4C:
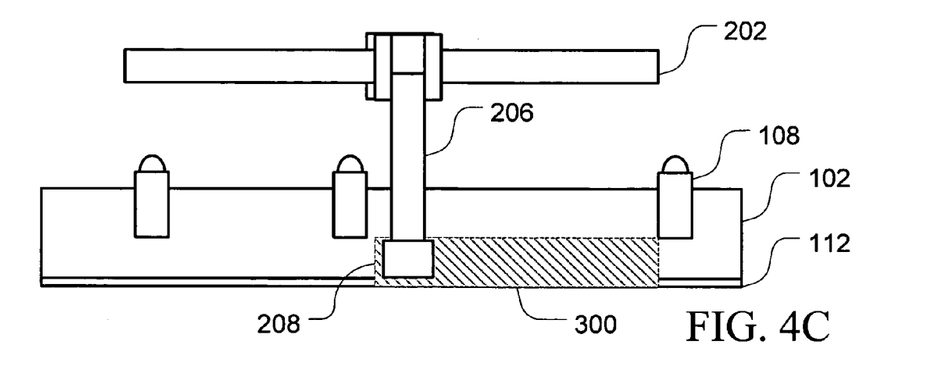

An exemplary scanning operation is illustrated in FIGS. 4A–C (with the shroud removed). As shown in FIG. 4A, the apparatus will be positioned adjacent the inner surface of the shroud 100 with the arcuate track 202 generally parallel the top surface of the core plate 102. The carrier 204 will be positioned above a portion of the annular gap 110 that is not obstructed by a core plate wedge 108. The sensor 208 portion of the apparatus will then be lowered into the annular gap 110 and positioned adjacent the weld or surface of interest. The sensor element or elements provided within the sensor 208 are then activated as the sensor is moved along the scanned feature to scan an area, generally suggested by area 300, and generate the desired scan data. This data is then analyzed to evaluate the condition of the scanned feature so that corrective action, if required, may be taken in a timely fashion. Additional guide and/or resilient elements (not shown) may be incorporated in the sensor support to allow a limited degree of passive "float" to accommodate minor irregularities in the scanned feature without damaging the sensor or requiring active vertical repositioning of the sensor support.

As will be appreciated, the scanning portions of the apparatus may be embodied in a wide variety of configurations, but will generally include an arcuate track 202 that is constructed to have a radius of curvature that this substantially identical to that of the inner surface of the shroud 100. Depending on the sizing of the annular gap 110, the lower portions of the sensor support 206 that will be inserted into the annular gap and one or more of the surfaces of the sensor 208 may also be configured with similar curvatures. By adapting these elements to better correspond to the annular gap 110, the likelihood of mechanical interference during the insertion into and movement along the gap may be reduced and the positioning mechanisms may be simplified. The apparatus may also include one or more stand-off elements 216 that will contact the inner surface of the shroud and positively establish a known offset for the arcuate track 202 relative to the shroud.

As illustrated in FIGS. 5A–D, the apparatus may be arranged within a casing or frame 212 that is configured to correspond to a fuel bundle assembly so that it may be inserted into the reactor core using the openings provided in the top guide and the corresponding alignment structures provided on the frame 212a and core plate 102 to fix the position of the frame relative to the inner surface of the shroud. During insertion and positioning of the frame 212, the scanning apparatus may be maintained in a protected or retracted position within the frame both to ease the insertion through the top guide and protect the more delicate elements of the apparatus. Once the frame has been positioned within the core, typically using a peripheral fuel bundle location, the scanning apparatus may be reconfigured to extend from the frame 212 and toward the inner surface of the shroud.

Figures 5A, 5B:
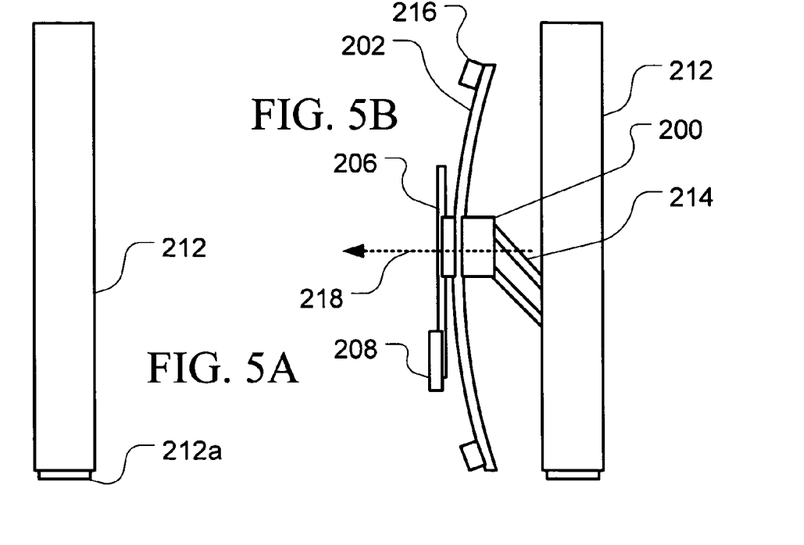
FIGS. 5A–D are views illustrating the operation of certain elements of an exemplary embodiment of the invention.
Figure 5C:
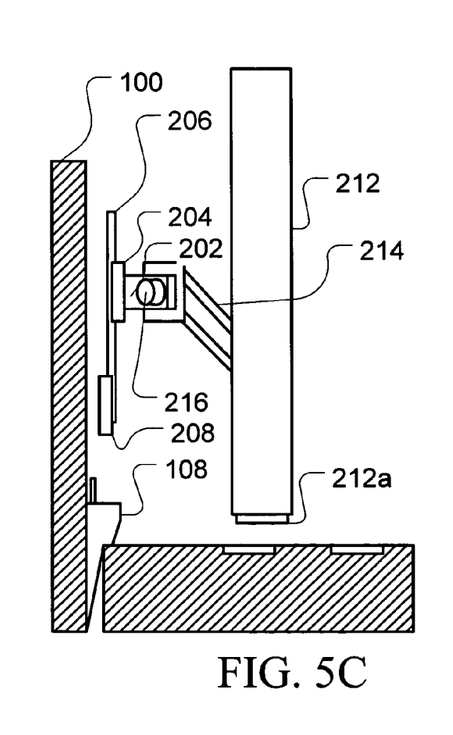
Figure 5D:
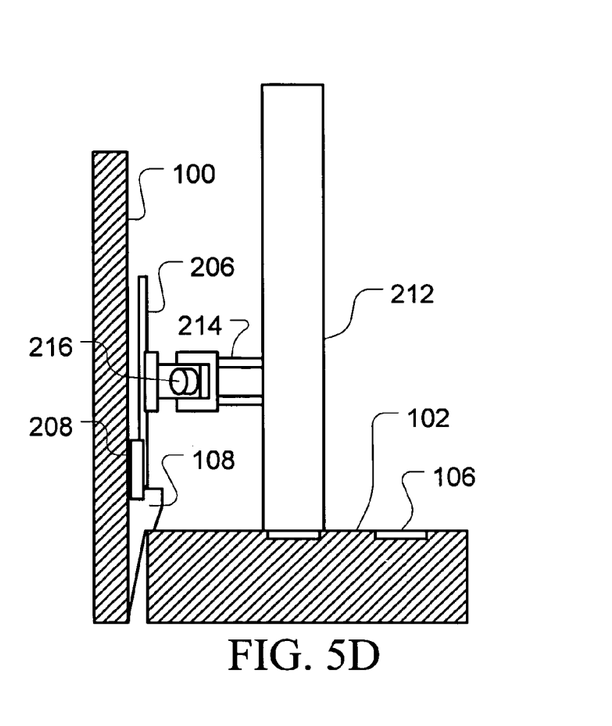

The arcuate track 202, which may be positioned in a substantially vertical orientation to fit within the frame 212, FIG. 5B, may then be rotated about an axis 218 to place it in a substantially horizontal configuration, FIG. 5C, i.e., substantially parallel to the top surface of the core plate, in preparation for the scanning operation. The extending portion of the scanning apparatus may be connected to the frame 212 using a variety of mechanical elements 214 and positioning elements including, for example, hydraulic pistons, pneumatic pistons, stepper motors, four-bar linkages that may be selected and configured to position the scanning apparatus adjacent the inner wall of the shroud 100 and above the annular gap 110 as illustrated in FIG. 5D.

Figures 6A, 6B:
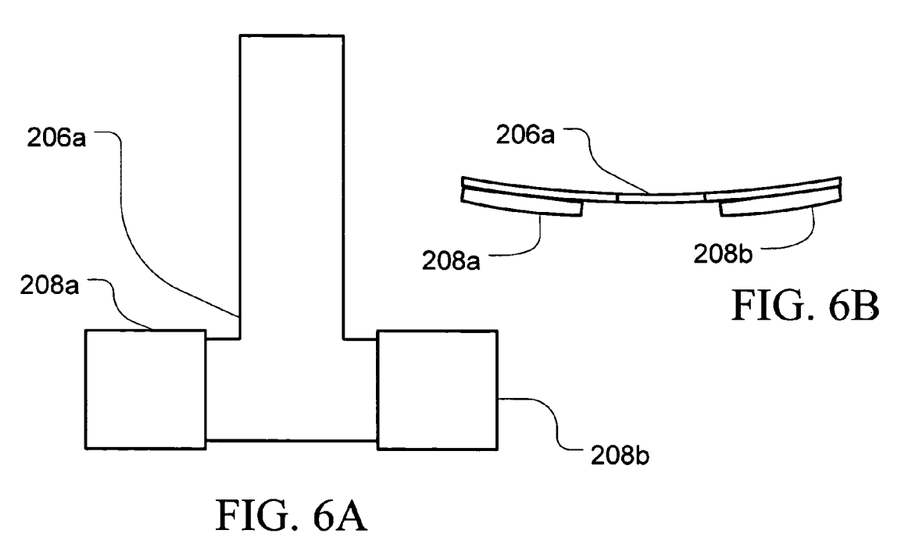
FIGS. 6A–D illustrate certain alternative configurations of a sensor arm and sensor head(s) that may be used with exemplary embodiments of the invention.
Figure 6C:
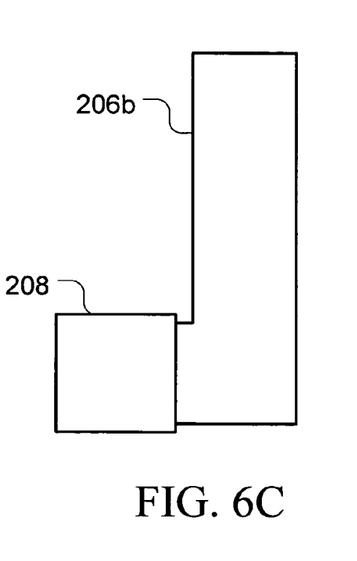
Figure 6D:
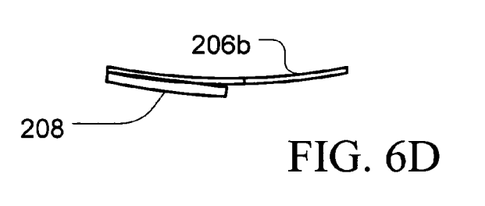

As illustrated in FIGS. 6A–D, the sensor support may be configured in a "T" shape, 206a, or an "L" shape, 206b, with sensors 208, 208a and 208b, provided on the extended portion(s) of the sensor supports. The use of such modified sensor supports in the scanning operation illustrated in FIGS. 4A–D, would allow the sensor head(s) to be positioned below the core plate wedges that limit the horizontal travel of the upper portion of the sensor support and increase the circumferential area that could be scanned using the exemplary apparatus. Further, as illustrated in FIGS. 6B and 6D, the sensor supports 206a, 206b and/or the sensors 208, 208a, 208b, may, depending on the relative sizing also be configured to correspond to the radius of curvature of the annular gap 110.

Figure 8:
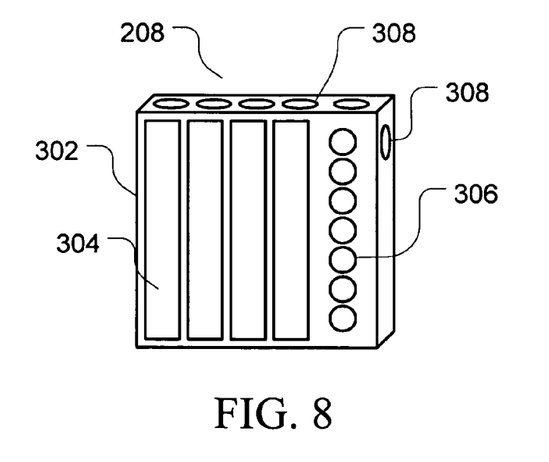
FIG. 8 illustrates an exemplary, multi-functional sensor head that may be used in practicing the invention.

As illustrated in FIG. 8, the sensor 208 may comprise a frame or main body 302 arranged for fastening to the sensor support and for holding a plurality of sensors 304, 306 that may have different configurations and/or be suitable for analyzing different properties of the scanned feature(s) or surfaces. For example, the sensor 208 may include a series of ultrasonic transducers configured to generate different frequency ranges and focused on different regions relative to the frame position. For example, the individual sensors in an exemplary sensor may include a 45° shear transducer operating at 2.25 MHz, a 60° refracted longitudinal (RL) transducer operating at 2.25 MHz, an outer diameter (OD) creeper transducer operating at 2.25 MHz and a 0° longitudinal transducer operating at 5 MHz. In order to accommodate the relatively narrow spacing of the annular gap 110, these transducers will typically have dimensions on the order of 5 mm to 21 mm, but, as will be appreciated, the actual sizing may be adapted to and will be determined by the particular application and the particular sensors being utilized in the sensor head. The sensor is not limited to ultrasonic devices and may include eddy current, electrical resistance, optical and other sensors as desired, provided that they can be configured to meet the space requirements. The frame 302 will also typically include a plurality connections or ports 308 for both power and sensing, communication or data lines that may include both conductive wires or cables and optical fiber lines.

Figure 7A:
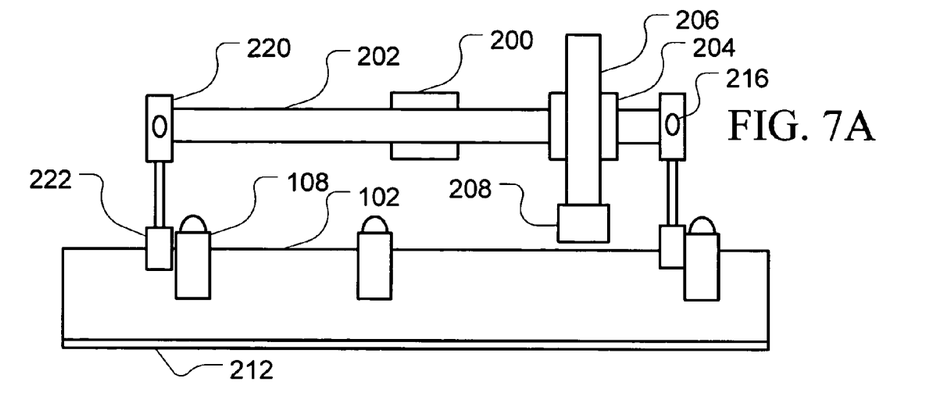
FIGS. 7A–C illustrate the operation of certain elements of another exemplary embodiment of the invention.
Figure 7B:
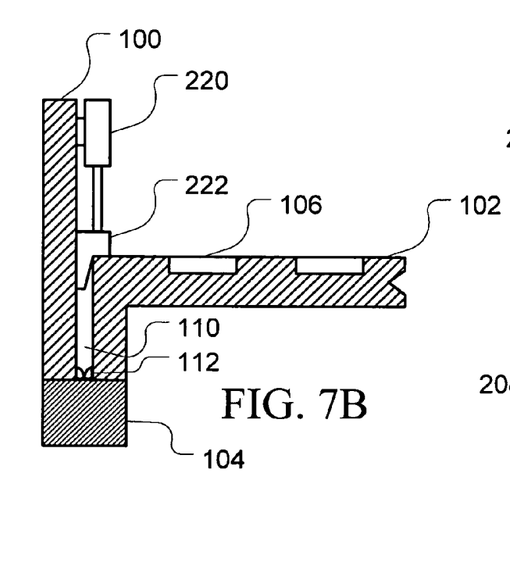

Other exemplary embodiments of apparatus according to the invention are illustrated in FIGS. 7A–C. As illustrated in FIG. 7A, the arcuate track 202 may be provided with holding devices arranged near the ends of the tracks. One embodiment of a holding device includes a cylinder 220 or other actuator that can be used to extend a positioning device such as a wedge 222, resilient member (not shown), cam (not shown) or other element. As illustrated in FIG. 7B, the positioning device(s) may be configured and may be positioned to temporarily fix the position of the track 202 with respect to the annular gap 110 by contacting one or more of the sidewalls of the annular gap, the inner surface of the shroud 100 and the core plate wedges 108 (not shown). Once the scanning operation has been completed, the positioning devices 222 may be released or withdrawn to allow for the repositioning of the scanning apparatus adjacent a different circumferential portion of the inner shroud 100.

Figure 7C:
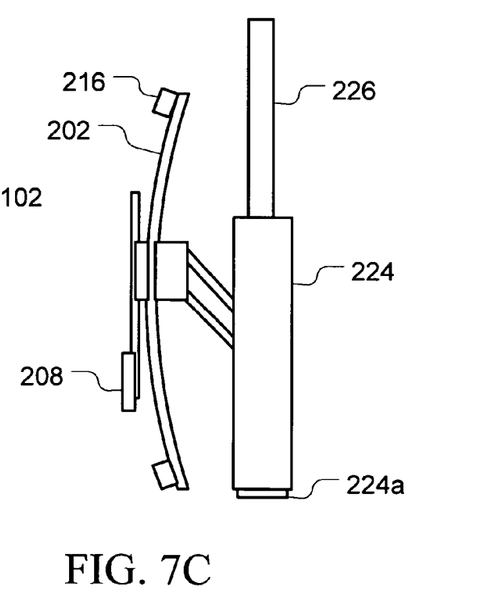

As illustrated in FIG. 7C, the scanning apparatus may be provided on a pole 226 that may support a frame or assembly 224 and allow for a wider range of movement within the reactor core. The frame 224 may also be provided with alignment structures 224a for positioning in fuel bundle locations on the core plate or may include other assemblies (not shown) for temporarily fixing the position of the scanning apparatus relative to the inner surface of the shroud 100. The other assemblies may be arranged and configured to connect to other hard points or attachment fixtures typically provided at various locations within the reactor vessel for conducting periodic maintenance. Alternatively, the other assemblies may be configured to interact with other structures typically arranged near the periphery of the core plate whereby the scanning apparatus may be temporarily fixed in position relative to the inner surface of the shroud. For example, vacuum assemblies may be provided for fixing the scanning apparatus to the shroud 100 or the core plate 102 by creating a pressure differential sufficient to hold the apparatus in place.

While this invention has been particularly shown and described with reference to exemplary embodiments thereof, it will be understood by those skilled in the art that various changes in form and details may be made therein without departing from the spirit and scope of the invention as defined by the appended claims.

We claim:

1. An apparatus for inspecting material within an annular recess comprising:
    a track support that may be positioned proximate the annular recess;
    a generally arcuate track provided on the track support, the track having a radius of curvature substantially identical to that of the annular recess;
    a carriage arranged and configured to move along the track in a first direction;
    a sensor support provided on the carriage and configured for movement along an axis substantially perpendicular to the first direction; and
    a sensor provided on the sensor support, the sensor being configured for insertion into the annual recess, whereby movement of the carriage causes the sensor to move along a portion of the surface of the annular recess.

2. An apparatus for inspecting material within an annular recess according to claim 1, further comprising:
    a holding mechanism for temporarily fixing the position of the track adjacent and above the annular recess.

3. An apparatus for inspecting material within an annular recess according to claim 2, wherein the holding mechanism includes one or more elements selected from a group consisting of:
    a stand-off element arranged to contact a surface extending from an outer sidewall of the annular recess for maintaining a predetermined spacing between the track and the surface;
    first and second actuators arranged proximate opposite ends of the track for positioning fastening elements within the annular recess;
    a vacuum assembly arranged for attachment to a surface extending from an outer sidewall of the annular recess; and
    a vacuum assembly arranged for attachment to a surface extending radially from the annular recess.

4. An apparatus for inspecting material within an annular recess according to claim 3, wherein the fastening elements include one or more elements selected from a group consisting of:
    a substantially wedge-shaped element configured for partial insertion into the annular recess in an insertion direction substantially perpendicular to the first direction for temporarily fixing the position of the inspecting apparatus relative the annular recess;

an asymmetric element having a first dimension less than a width of the annular recess and a second dimension at least equal to the width of the annular recess configured for rotation for temporarily fixing the position of the inspecting apparatus relative the annular recess;

a resilient element that assumes a compressed configuration as it is inserted into the annular recess; and an element configured for selective transition between an enlarged configuration and a reduced configuration for temporarily fixing the position of the inspecting apparatus relative the annular recess.

5. An apparatus for inspecting material within an annular recess according to claim 1, further comprising:

a housing, the housing arranged and configured to contain the track support, the generally arcuate track, the carriage, the sensor support and the sensor in a stored configuration.

6. An apparatus for inspecting material within an annular recess according to claim 5, further comprising:

a housing, the housing arranged and configured to contain and protect the track support, the generally arcuate track, the carriage, the sensor support and the sensor when in a stored configuration; and a deployment mechanism arranged for selectively extending the track support, the generally arcuate track, the carriage, the sensor support and the sensor from the housing when in a deployed configuration and returning to the stored configuration.

7. An apparatus for inspecting material within an annular recess according to claim 6, wherein:

the deployment mechanism is arranged for the selective rotation of the track between a substantially vertical orientation and a substantially horizontal orientation.

8. An apparatus for inspecting material within an annular recess according to claim 5, wherein:

an orientation of the track support is substantially identical in both the stored and deployed configurations.

9. An apparatus for inspecting material within an annular recess according to claim 8, wherein:

the deployment mechanism includes a four-bar linkage for maintaining the orientation of the track support as it moves between the stored and deployed configurations.

10. An apparatus for inspecting material within an annular recess according to claim 1, wherein:

the sensor support includes an upper connecting portion and a lower sensor supporting portion, the supporting portion having a horizontal extension that exceeds a horizontal extension of the connecting portion.

11. An apparatus for inspecting material within an annular recess according to claim 10, wherein:

the horizontal extension of the supporting portion exceeds the horizontal extension of the connecting portion in two directions.

12. An apparatus for inspecting material within an annular recess according to claim 1, wherein:

the sensor includes a plurality of ultrasonic transducers.

13. An apparatus for inspecting material within an annular recess according to claim 12, wherein:

the plurality of ultrasonic transducers are configured to emit at least two frequencies and focused in at least two directions.

14. An apparatus for inspecting material within an annular recess according to claim 13, wherein:

the frequencies include a first frequency of between about 2 and about 2.5 MHz and a second frequency between about 4.5 and about 5.5 MHz.

15. A method for inspecting material within an annular recess using an apparatus configured according to claim 1, the method comprising the steps of:

orienting and aligning the generally arcuate track above the annular recess;

extending a portion of the sensor support and sensor into the annular recess;

activating the sensor for generating data corresponding to a condition of the material; and moving the carriage along the track, to thereby moving the sensor along an arcuate portion of the material.

16. A method for inspecting material within an annular recess according to claim 15, wherein:

the annular recess is formed within a nuclear reactor between an inner surface of a shroud and an outer circumferential surface of a core plate.

17. A method for inspecting material within an annular recess according to claim 16, wherein:

the material includes a portion of a weld bead.

18. A method for inspecting material within an annular recess according to claim 17, wherein:

the weld bead is the H6A weld bead.

19. An apparatus for inspecting material within an annular recess according to claim 1, further comprising:

a holding mechanism for engaging at least one fixed surface adjacent the annular recess to fix a temporary position of the track adjacent and above the annular recess.

20. An apparatus for inspecting material within an annular recess according to claim 1, wherein:

the generally arcuate track corresponds to only a minor portion of a circumference of the annular recess.

* * * * *